United States Patent
Park et al.

(10) Patent No.: US 8,551,791 B2
(45) Date of Patent: Oct. 8, 2013

(54) APPARATUS AND METHOD FOR MANUFACTURING SEMICONDUCTOR DEVICES THROUGH LAYER MATERIAL DIMENSION ANALYSIS

(75) Inventors: Jang-Ik Park, Suwon-si (KR); Chung-Sam Jun, Suwon-si (KR); Hwan-Shik Park, Seoul (KR); Ji-Hye Kim, Anyang-si (KR); Kwan-Woo Ryu, Hwaseong-si (KR); Kong-Jung Sa, Hwaseong-si (KR); So-Yeon Yun, Hwaseong-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 1140 days.

(21) Appl. No.: 12/457,873

(22) Filed: Jun. 24, 2009

(65) Prior Publication Data
US 2009/0325326 A1 Dec. 31, 2009

(30) Foreign Application Priority Data
Jun. 25, 2008 (KR) .................. 10-2008-0059983

(51) Int. Cl.
*H01L 21/00* (2006.01)
*G06K 9/00* (2006.01)
*G01N 21/00* (2006.01)

(52) U.S. Cl.
USPC .............................. 438/7; 382/149; 356/237.5

(58) Field of Classification Search
USPC .............. 438/7, 16; 257/E21.53; 356/237.5, 356/498; 382/149
See application file for complete search history.

(56) References Cited

U.S. PATENT DOCUMENTS

| | | | |
|---|---|---|---|
| 6,221,679 B1 * | 4/2001 | Smith et al. | 438/7 |
| 6,630,995 B1 * | 10/2003 | Hunter | 356/237.5 |
| 6,829,559 B2 * | 12/2004 | Bultman et al. | 702/155 |
| 7,167,242 B2 | 1/2007 | Nabatova-Gabain et al. | |
| 7,196,793 B2 | 3/2007 | Nabatova-Gabain et al. | |
| 7,274,472 B2 * | 9/2007 | Bischoff | 356/635 |
| 7,443,512 B2 | 10/2008 | Kim et al. | |
| 7,999,940 B2 * | 8/2011 | Kok | 356/445 |

FOREIGN PATENT DOCUMENTS

| | | |
|---|---|---|
| JP | 10-010041 A | 1/1998 |
| KR | 10-0393522 B1 | 7/2003 |
| KR | 10-2004-0048405 A | 6/2004 |
| KR | 10-2005-0096847 A | 10/2005 |

OTHER PUBLICATIONS

Henning Rust, "Spectral Analysis of Stochastic Processes", Lecture Notes for the E2C2/CIACS Summer School, Comorova, Romania, University of Potsdam, pp. 1-76.*

* cited by examiner

*Primary Examiner* — William D Coleman
(74) *Attorney, Agent, or Firm* — Lee & Morse, P.C.

(57) ABSTRACT

Apparatus and method for manufacturing a semiconductor device through a layer material dimension analysis increase productivity. The method includes performing a semiconductor manufacturing process of at least one reference substrate and at least one target substrate in a semiconductor process device, detecting a reference spectrum and a reference profile for the reference substrate, determining a relation function between the detected reference spectrum and reference profile, detecting a real-time spectrum of the target substrate, and determining in real time a real-time profile of the target substrate processed in the semiconductor process device by using the detected real-time spectrum as a variable in the determined relation function.

20 Claims, 25 Drawing Sheets

FIG. 4

$$\underline{w} \text{ FIXED VALUE} \times \underline{x} \text{ SPECTRUM} + \underline{b} \text{ CONSTANT VALUE} = \underline{y} \text{ SOLUTION}$$

$$\begin{pmatrix} w_{11} & w_{12} & w_{13} & \dots \\ w_{21} & w_{22} & w_{23} & \dots \\ & \dots & & \end{pmatrix} \times \begin{pmatrix} x_{11} & x_{12} & x_{13} & \dots \\ x_{21} & x_{22} & x_{23} & \dots \\ & \dots & & \end{pmatrix} + \begin{pmatrix} b_{11} & b_{12} & b_{13} & \dots \\ b_{21} & b_{22} & b_{23} & \dots \\ & \dots & & \end{pmatrix} = \begin{pmatrix} y_{11} & y_{12} & y_{13} & \dots \\ y_{21} & y_{22} & y_{23} & \dots \\ & \dots & & \end{pmatrix}$$

APPARATUS AND METHOD FOR MANUFACTURING SEMICONDUCTOR DEVICES THROUGH LAYER MATERIAL DIMENSION ANALYSIS

BACKGROUND OF THE INVENTION

1. Field of the Invention

Example embodiments relate to a semiconductor device manufacturing method and apparatus. More particularly, example embodiments relate to a method for manufacturing a semiconductor device through a dimension analysis of layer material formed on a semiconductor substrate, and to an apparatus employing the same.

2. Description of the Related Art

An optical critical dimension (OCD) technology refers to techniques of acquiring information of a semiconductor substrate surface through a polarized light state change.

For example, the OCD technology may be realized by analyzing, e.g., via a Rigorous Coupled Wave Analysis (RCWA) principle, a spectrum acquired through use of an optical device, e.g., a spectroscopic ellipsometer (SE) or a spectroscopic reflectometer (SR), from a regular pattern, e.g., a pattern having a size on a scale of tens nanometers to hundreds of nanometers. The OCD technology may be used to analyze a profile of such a pattern to measure, e.g., a thickness of pattern, critical dimension (CD), height, recess, roughness, and so forth.

A conventional layer material dimension analysis method using the RCWA principle may perform the Fourier transform of a spectrum measured from the regular pattern, and may process and manage it as a profile parameter through Maxwell equations.

However, while the conventional layer material dimension analysis may be performed for a two-dimensional computation, e.g., of line/space structure, of the regular pattern, the conventional layer material dimension analysis may be complex for a three-dimensional computation, e.g., of an island structure, of the regular pattern. In particular, the Fourier transform and Maxwell equations may be complicated for a three-dimensional structure, and may require a long computational time, e.g., computation and analysis of a three-dimensional structure may be about 100 times longer than computation and analysis of a two-dimensional structure via the Fourier transform and Maxwell equations. Therefore, the conventional layer material dimension analysis may have a limited application with respect to a three-dimension pattern, so monitoring of a semiconductor manufacturing process in real time may be complicated.

SUMMARY OF THE INVENTION

Embodiments are therefore directed to a semiconductor device manufacturing method and apparatus, which substantially overcome one or more of the problems due to the limitations and disadvantages of the related art.

It is therefore a feature of an embodiment to provide a semiconductor manufacturing apparatus and method capable of substantially increasing productivity by facilitating a profile computation of a three dimensional pattern.

It is therefore another feature of an embodiment to provide a semiconductor manufacturing apparatus and method capable of substantially reducing a required time for obtaining a profile of a three dimensional pattern, thereby enabling real time monitoring.

At least one of the above and other features and advantages may be realized by providing a semiconductor manufacturing apparatus, including a semiconductor process device performing a semiconductor manufacturing process on substrates to be processed, a reference spectrum analysis system detecting a reference spectrum and a reference profile for a substrate determined as a reference substrate among the substrates, and then acquiring a related function between the detected reference spectrum and the reference profile, and a real-time spectrum analysis system detecting a real-time spectrum of a substrate determined as an observed substrate among the substrates, and then detecting in real time a profile of the observed substrate processed in the semiconductor process device by applying the real-time spectrum to the function.

Here, the reference spectrum analysis system may include an optical device to detect the reference spectrum from a light reflected by irradiating an incident light onto a surface of the reference substrate, a measurement device to measure a reference profile of a surface of the reference substrate, and a reference spectrum analysis server to acquire the function between the reference spectrum and the reference profile. The reference spectrum analysis server may acquire a linear function when a deposition process of the substrates is performed in the semiconductor process device and acquire an exponential function when an etching process of the substrates is performed in the semiconductor process device.

At least one of the above and other features and advantages may also be realized by providing a method of manufacturing a semiconductor device, including performing a semiconductor manufacturing process of substrates to be processed, detecting a reference spectrum and a reference profile for a substrate determined as a reference substrate among the substrates; acquiring a related function between the reference spectrum and the reference profile, detecting a real-time spectrum of a substrate determined as an observed substrate among the substrates, and detecting in real time a profile of the observed substrate processed in the semiconductor process device by applying the real-time spectrum as a variable to the function.

Here, the profile of the observed substrate may correspond to a solution of the function having the real time spectrum as a variable, and the function may comprise at least one of linear function (primary function), quadratic function, higher-order function, fraction function, trigonometric function, exponential function and logarithmic functions. The linear function may be used for a detection of profile corresponding to a thickness of layer material formed on the substrates, and the exponential function may be used for a detection of profile corresponding to a recess or CD of layer material formed on the substrates.

At least one of the above and other features and advantages may also be realized by providing a method of analyzing a dimension of layer material, including performing a semiconductor manufacturing process processing substrates, irradiating an incident light onto a surface of the substrate by a given degree, acquiring a spectrum of reflected light reflected from the surface of the substrate, acquiring a solution of predetermined function by using the spectrum as a variable, and monitoring a surface state of the substrate by using the solution of the function.

BRIEF DESCRIPTION OF THE DRAWINGS

The above and other features and advantages will become more apparent to those of ordinary skill in the art by describing in detail exemplary embodiments with reference to the attached drawings, in which:

FIG. 4 illustrates an acquirement of a solution of a linear function using a spectrum in a real-time spectrum analysis server;

DETAILED DESCRIPTION OF THE INVENTION

Figure 1:
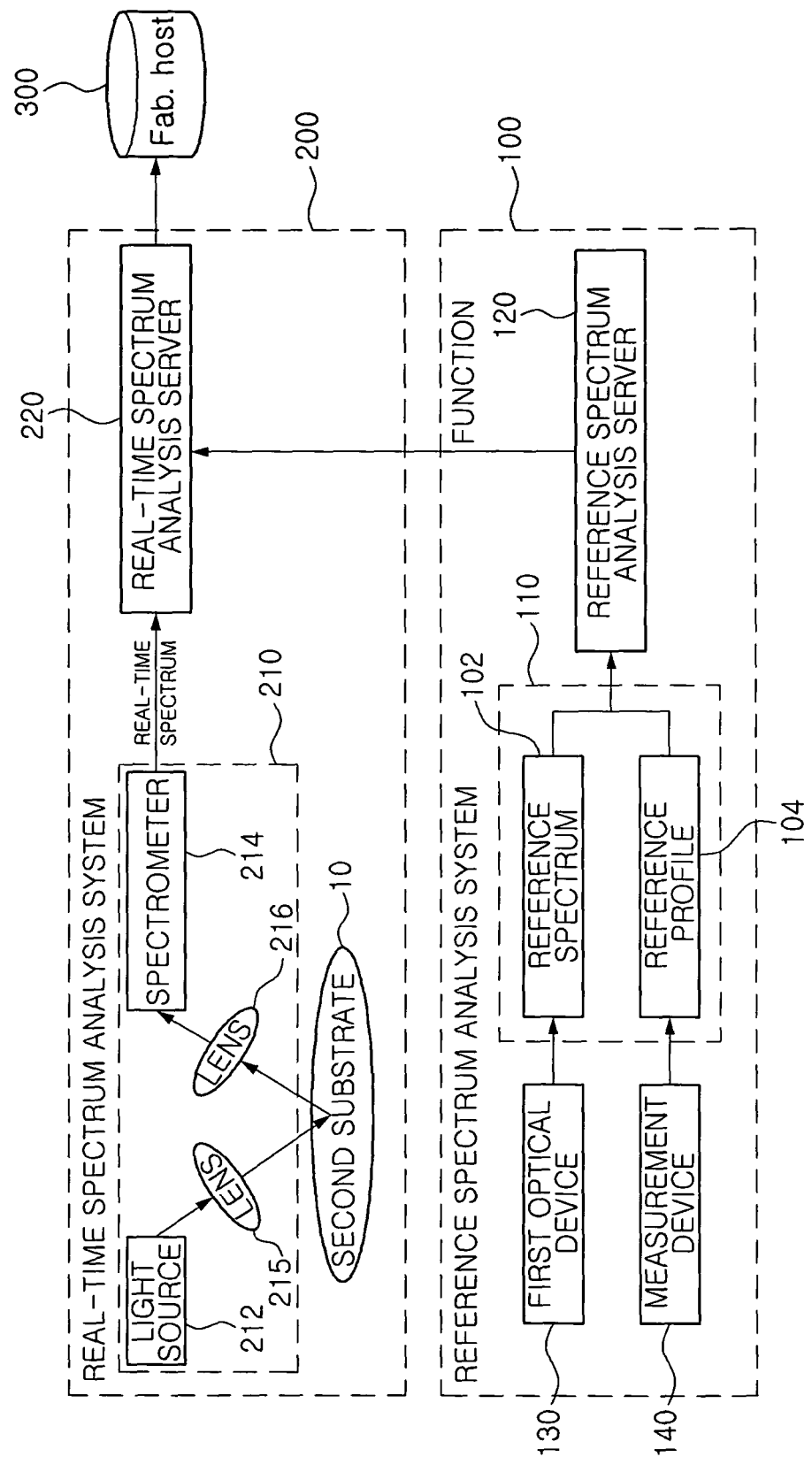
FIG. 1 illustrates a schematic layer-material dimension analysis system according to an embodiment.

Korean Patent Application No. 10-2008-0059983, filed on Jun. 25, 2008, in the Korean Intellectual Property Office, and entitled: "Apparatus and Method for Manufacturing Semiconductor Devices Through Layer Material Dimension Analysis," is incorporated by reference herein in its entirety.

Unless otherwise defined, all terms (including technical and scientific terms) used herein have the same meaning as commonly understood by one skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein. Embodiments are more fully described below with reference to the accompanying drawings. This invention may, however, be embodied in many different forms and should not be construed as being limited to the embodiments set forth herein; rather, these embodiments are provided so that this disclosure is thorough and complete, and conveys the inventive concept to those skilled in the art.

In the drawing figures, relative dimensions of elements and regions may be exaggerated for clarity of illustration. It will also be understood that when an element is referred to as being "connected to" or "transmitting to" another element, the elements may be connected directly, or intervening elements may be present. Like reference numerals refer to like elements throughout. As used herein, the expressions "at least one," "one or more," and "and/or" are open-ended expressions that are both conjunctive and disjunctive in operation.

FIG. 1 schematically illustrates a layer-material dimension analysis system according to an embodiment.

Referring to FIG. 1, a layer-material dimension analysis system according to an embodiment may employ an empirical spectrum analysis (ESA) technology and may include a reference spectrum analysis system 100 and a real time spectrum analysis system 200. The reference spectrum analysis system 100 may compute a function relation, i.e., a function denoting a relation between spectrum and profile of a reference layer material, and the real time spectrum analysis system 200 may detect a spectrum of a real-time layer material, e.g., during or immediately after processing thereof, and may determine a profile of the processed layer material in real time by using the detected spectrum of the real-time layer material in the relation function computed by the reference spectrum analysis system 100. Accordingly, in a layer material dimension analysis system according to an embodiment of the invention, a spectrum of a processed layer material, i.e., a layer material during processing or immediately after processing, may be detected in real-time by using a previously determined function acquired through reference information, and further a profile of the processed layer material may be detected in real time, thereby substantially increasing productivity.

Referring to FIG. 1, the reference spectrum analysis system 100 may include a database 110 with a reference profile 104 and a reference spectrum 102, and a reference spectrum analysis server 120. First, a reference layer material may be formed on a reference substrate, i.e., a first substrate (not shown), manufactured through a semiconductor manufacturing process of interest. Then, the reference spectrum analysis system 100 may determine the function relation of the reference material layer by using the reference profile 104 and the reference spectrum 102 on the reference layer material. The reference spectrum 102 and the reference profile 104 may be stored as reference in the database 110. The reference spectrum analysis server 120 may provide the function relation of the reference material layer based on a correlation between the reference profile 104 and the reference spectrum 102 stored in the database 110.

For example, the reference spectrum 102 may be acquired by a first optical device 130. The first optical device 130, e.g., a SE, may detect light reflected from a surface of the reference layer material, e.g., reflection angle, by irradiating light on the reference layer material at a predetermined degree, e.g., incidence angle. A detailed method for obtaining the reference spectrum 102 will be described below. The reference profile 104 may include information of a state of the reference layer material, e.g., thickness, size, height, recess, etc., on the reference substrate. The reference profile 104 may be acquired by a measurement device 140, e.g., an electron microscope. Further, the reference profile 104 may be acquired by using the reference spectrum 102, e.g., through a conventional OCD method using Furrier conversion and Maxwell equation.

As the reference profile 104 may be calculated and obtained by using the reference spectrum 102, it may be possible to gain a proportioned or circulated/repeated function relation between the reference spectrum 102 and the reference profile 104. As described above, the reference spectrum analysis server 120 may determine a function based on a correlation between the reference spectrum 102 and the reference profile 104. The function determined in the reference spectrum analysis server 120 may include, e.g., a linear function (primary function), a quadratic function, a higher-order function, a fraction function, a trigonometric function, an exponential function, and a logarithmic function according to kinds of processes performed during semiconductor manufacturing. For example, the function determined in the reference spectrum analysis server 120 may be a polynomial function, e.g., as shown in Equation 1 below.

$$y=f(wx+b) \qquad \text{Equation 1}$$

In Equation 1 above, x is a variable corresponding to the reference spectrum 102, y is a variable corresponding to the reference profile 104, 'w' is a fixed value, and 'b' is a constant value. The reference spectrum and profile 102 and 104 may be detected with respect to the reference substrate, and the fixed and constant values 'w' and 'b' may be obtained as will be discussed in detail below with reference to FIG. 6-16C. Thus, the reference spectrum analysis system 100 may determine a function f correlating the reference spectrum 102 and the reference profile 104 by using the reference spectrum analysis server 120.

As further illustrated in FIG. 1, the real-time spectrum analysis system 200 may include a second optical device 210 and a real-time spectrum analysis server 220. The real-time spectrum analysis system 200 may determine in real time a profile of a real-time layer material, e.g., a second substrate 10, based on a real-time spectrum of the real-time layer material and the function relation determined in the reference spectrum analysis system 100. The second substrate 10 may be fabricated through a substantially same or similar semiconductor manufacturing process as the reference substrate. Here, the second substrate 10 may be, e.g., a substrate measured for a real-time spectrum or a substrate supporting a layer material to be measured for the real-time spectrum, and may be compared to the reference substrate or a mass-production substrate produced in a large quantity in a production line.

For example, the real-time spectrum analysis system 200 may include the second optical device 210 to acquire a real-time spectrum from a surface of the second substrate 10. The real-time spectrum analysis server 220 may acquire a profile of the real-time layer material on the surface of the second substrate 10 by applying the real-time spectrum of the second substrate 10 to the function relation from the reference spectrum analysis server 120. In other words, the function f determined by the reference spectrum analysis server 120 and the variable x, i.e., in this case the real-time spectrum as acquired from the second optical device 210, may be implemented in Equation 1 by the real-time spectrum analysis server 220 in order to solve Equation 1 for y, i.e., the real-time profile of the second substrate 10. Here, the second optical device 210 may be substantially the same as the first optical device 130, with the exception of the type of spectrum obtained, i.e., the first optical device 130 may obtain a reference spectrum while the second optical device 210 may obtain a real-time spectrum. Thus, only the second optical device 210 will be described in detail hereinafter.

In the second optical device 210, an incident light generated from a light source 212 may be irradiated at a predetermined angle on the surface of the second substrate 10. The second substrate 10 may be horizontally supported on a stage (not shown), and a spectrometer 214 may receive a spectrum of light reflected from the surface of the second substrate 10. An optical system may be further included in the second optical device 210, e.g., the optical system may include a first lens 215 concentrating and projecting the incident light generated from the light source 212 and a second lens 216 enlarging and projecting light reflected from the second substrate 10. Though not shown, the optical system may further include at least one circular polarizing plate or elliptical polarizing plate polarizing an electromagnetic wave of the incident light generated in the light source 212 into a circularly or elliptically polarized light.

Here, the light source 212 may include, e.g., a Xenon lamp generating a visible light having a wavelength of about 3000 Å to about 7000 Å. The spectrometer 214 may acquire the real-time spectrum based on a frequency or wavelength of light reflected from the surface of the second substrate 10 by using a difference of refraction rate based on the wavelength of light. The spectrometer 214 may measure a real-time spectrum for a real-time layer material having a thickness of about 500 Å or more. When a thickness of the real-time layer material, i.e., a target layer material, is too thin, e.g., about 500 Å or less, the difference of the refraction rate as determined by the spectrometer 214 during the spectrum measurement may be great and interference between light reflected from the surface of the second substrate 10 and light reflected inside of the real-time layer material may be reduced. Thus, a spectrum measured with respect to layer having a thickness of about 500 Å or less may be unclear and include a relatively high number of measurement errors. Therefore, when a thickness of the real-time layer material is sufficiently thick, e.g., about 500 Å or more, the refraction rate of the real-time layer material may be uniform with a given level, interference between light reflected from the surface of the second substrate 10 and light reflected inside of the real-time layer material may be increased, and thus, the spectrum may be clear. Therefore, a measurement error may be reduced.

In detail, the spectrometer 214 may determine the real-time spectrum of the real-time layer material by measuring changes in each of a ratio degree ($\psi$) and a phase degree ($\Delta$) of the light reflected from the surface of the second substrate 10, e.g., by using the double refraction to detect in high resolution minute structures, i.e., small size on a nano-scale, on the surface of the second substrate 10, e.g., a contact hole, a trench, and/or a line/space. The ratio degree ($\psi$) refers to Euler angle of a ratio between a reflected longitudinal wave (P wave component of the reflected light) having mutually coinciding progression direction and vibration direction and a transverse wave (S wave component of the reflected light) for which the progression direction is vertical to the vibration direction. The phase degree ($\Delta$) refers to a Euler angle of a phase shift between the longitudinal wave (P wave) and the transverse wave (S wave).

Figure 2A:
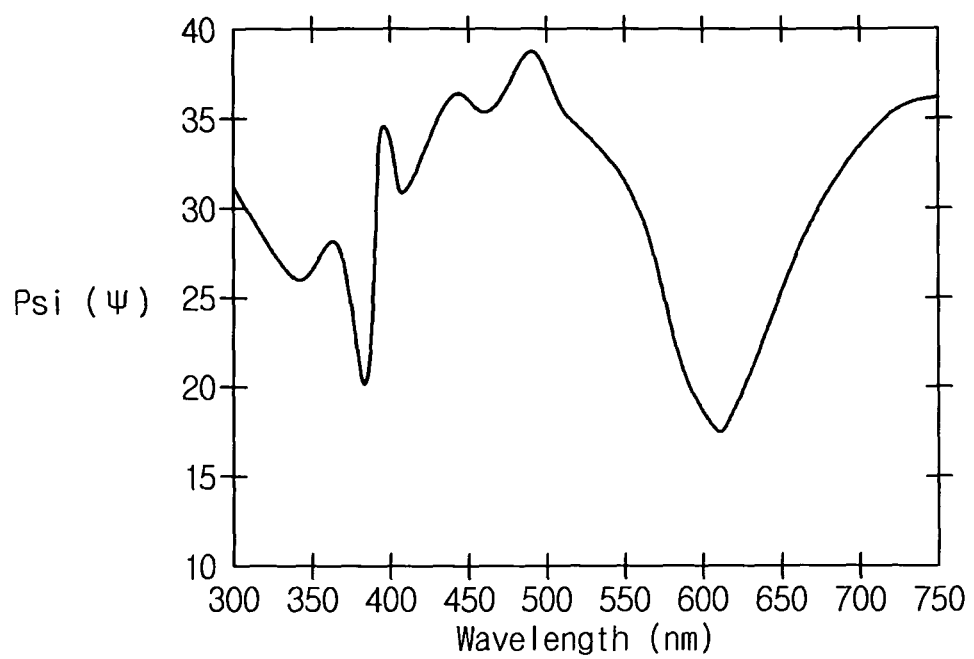
FIGS. 2A and 2B illustrate exemplary spectra detected in a spectrometer of FIG. 1.
Figure 2B:
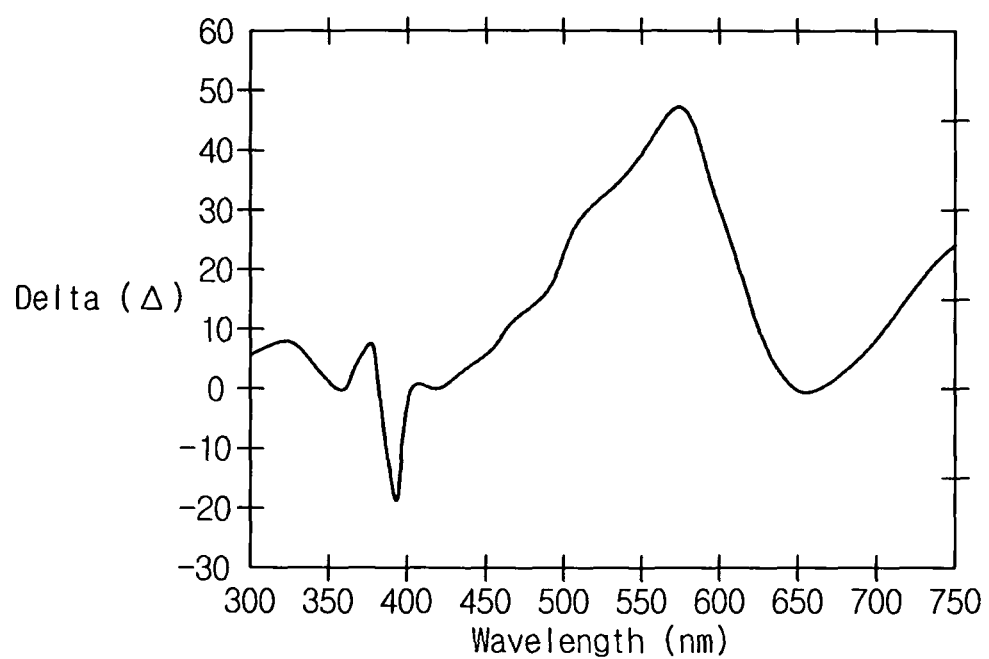

FIGS. 2A and 2B illustrate real-time spectra as detected by the spectrometer 214 of FIG. 1. In particular, FIGS. 2A and 2B illustrate variation in ratio degree ($\psi$) and phase degree ($\Delta$), respectively, according to wavelength. The spectra in FIGS. 2A and 2B exhibit oscillation according to a refraction rate and reflection rate provided in kinds and state of the real-time layer material formed on the surface of the second substrate 10. Here, an X-axis has a unit of nm as a wavelength band of visible light with a range of 300 nm to 750 nm. A Y-axis indicates a unit of degree for a spectrum of visible light band.

Referring to FIGS. 2A and 2B, the ratio degree ($\psi$) had an oscillation with varying amplitude within a range of about 15 degrees to about 40 degrees, and the phase degree ($\Delta$) had an oscillation with varying amplitude within a range of about (−30) degrees to about 50 degrees. Since a category of oscillation in FIG. 2A was small, a measurement error for the obtained real-time spectrum based on a change of the refraction rate may be reduced. Accordingly, in embodiments, a profile of the surface of the second substrate 10 may be calculated using a real-time spectrum corresponding to the ratio degree ($\psi$). Thus, a measurement error range in determining the profile of the second substrate 10 may be relatively small.

As described above, the real-time spectrum analysis server 220 may calculate a solution of function provided from the reference spectrum analysis server 120, i.e., i.e., y in the Equation 1, with the real-time spectrum, as determined by the spectrometer 214, as a variable, i.e., x in the Equation 1. The real-time spectrum analysis server 220 may receive various kinds of functions f from the reference spectrum analysis server 120, e.g., the functions f transmitted from the reference spectrum analysis server 120 may depend on a semiconductor process of the second substrate 10.

For example, a solution, i.e., y in the Equation 1, corresponding to a profile of the real-time layer material thickness may be obtained by using a linear function, i.e., f in Equation 1, in a deposition process forming a thin film on the second substrate 10. In another example, when the second substrate 10 is processed via an etching process, a solution corresponding to a profile of, e.g., a CD, a height, a recess, roughness, etc. of the second substrate 10, may be obtained by using an exponential function. The real-time spectrum analysis server 220 may calculate a solution of the function f with respect to the variable x, i.e., the real-time spectrum determined with respect to the second substrate 10 during or promptly after a semiconductor manufacturing process, and then may output the solution to a host computer 300.

Accordingly, the host computer 300 may monitor in real time a drive state of corresponding semiconductor process device. In particular, the analysis result obtained in the layer-material dimension analysis system, i.e., the solution obtained by the real-time spectrum analysis server 220, may be provided to the host computer 300, and then may be transmitted to a semiconductor manufacturing apparatus, i.e., an apparatus processing the second substrate 10, to influence processing of the second substrate 10, e.g., processing of the second substrate 10 may be continued or aborted in real time due to characteristics of its surface as determined by the real-time spectrum analysis server 220.

Therefore, a layer material analysis system according to an embodiment may calculate a solution for a function that uses as a variable a real-time spectrum, i.e., acquired from the surface of the second substrate 10 during or immediately after processing thereof. The solution may correspond to a surface profile of the second substrate 10, thereby providing a relatively simple calculation of a three-dimensional profile as well as a two-dimensional profile. Additionally, since the three three-dimensional profile determination and analysis may be performed in real-time, efficiency and productivity of the semiconductor manufacturing process may be substantially increased.

The layer material dimension analysis system may be included in a semiconductor manufacturing apparatus, together with the host computer 300 monitoring a general flow of semiconductor manufacturing process including a spectrum analysis and a semiconductor process device controlled by the host computer 300 and performing a semiconductor manufacturing process. Furthermore, embodiments of the invention may be enlarged and applied to a semiconductor production line analyzing and managing a dimension of layer material formed through the general process of semiconductor production.

With such configuration, a layer material dimension analysis system and a method of analyzing a layer material dimension by using a semiconductor manufacturing apparatus are described in detail as follows. For reference, an analysis method of the real-time spectrum analysis system 200 will be first described to help understand the layer material dimension analysis method using the real-time spectrum, and then an analysis method of the reference spectrum analysis system 100 will be described.

Figure 3:
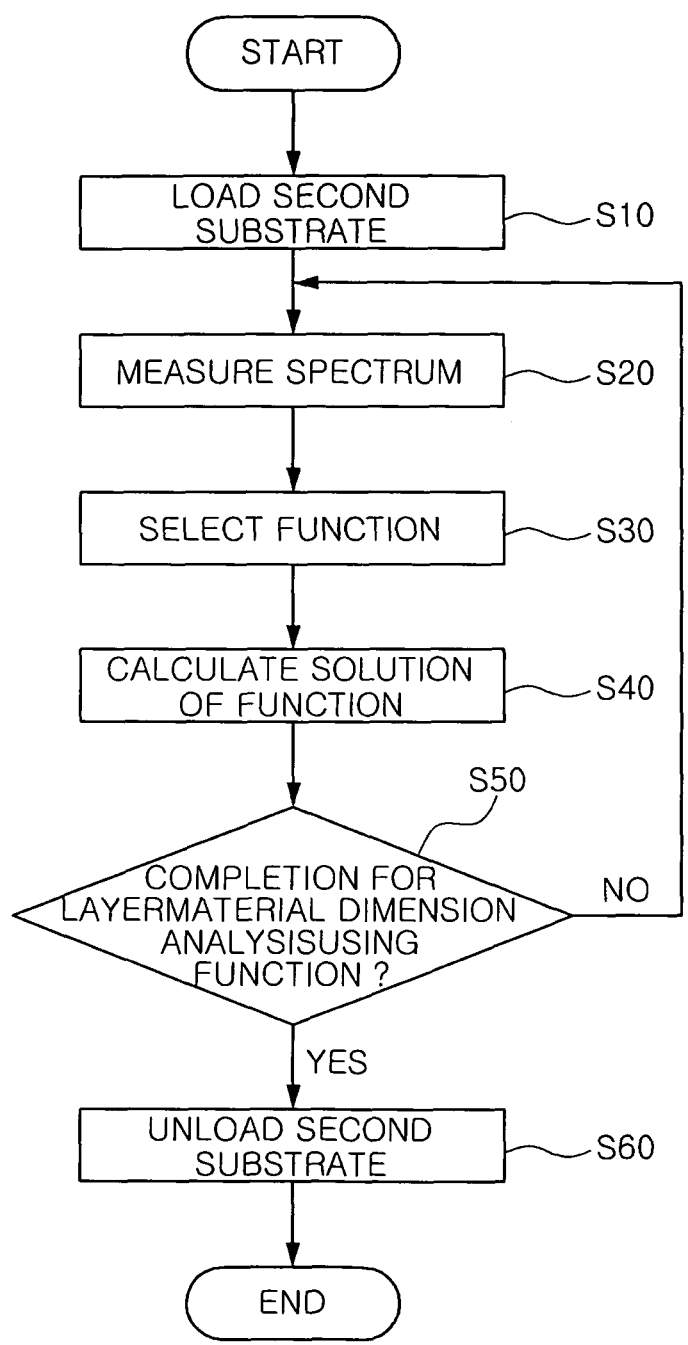
FIG. 3 illustrates a flowchart of a method for performing a layer material dimension analysis in a real-time spectrum analysis system according to an embodiment.

FIG. 3 illustrates a flowchart schematically providing a layer material dimension analysis method for use in the real-time spectrum analysis system 200 according to an embodiment.

As shown in FIG. 3, in a layer material dimension analysis method according to an embodiment, the second substrate 10 may be loaded in operation S10, e.g., loaded on a stage during processing or immediately after completion of a given semiconductor manufacturing process, so as to enable the surface measurement of the second substrate 10 through the second optical device 210.

Then, the second optical device 210 may project at a predetermined angle an incident light generated from light source 212 onto a corresponding position of the surface of the second substrate 10, and may detect light reflected from the surface of second substrate 10. Thus, the second optical device 210 may acquire the real-time spectrum of the surface of the second substrate 10 based on the reflected light from the second substrate 10 in operation S20. At this time, the second optical device 210 may detect the real-time spectrum of the second substrate 10, varying a wavelength of the incident light. For example, the incident light may be visible light having a wavelength of about 300 nm to about 750 nm, and may be emitted from a Xenon lamp. The incident light may be irradiated on the second substrate 10 at an incident angle of about 15 degrees to about 45 degrees with respect to the surface of the second substrate 10, and may be reflected in a direction of about 360 degrees with respect to the second substrate 10. The spectrometer 214 may receive the light reflected from the surface of second substrate 10 and, thus, may detect the ratio degree ($\psi$) and the phase degree ($\Delta$).

Then, the real-time spectrum analysis server 220 may select and receive from the reference spectrum analysis server 120 a function corresponding to a specific semiconductor manufacturing process performed on the second substrate 10, i.e., operation S30. In operation S40, the real-time spectrum analysis server 220 may obtain a solution for the function received in operation S30 by using the spectrum acquired from the second optical device 210 with respect to the second substrate 10 in operation S20. As described above, the real-time spectrum analysis server 220 may select mutually different kinds of functions according to kinds of semiconductor manufacturing processes to process the second substrate 10, and may calculate a solution of the function corresponding to a characteristic of the surface of the second substrate 10. For example, the real-time spectrum analysis server 220 may obtain the solution of a function by using a single spectrum of a specific single wavelength, and/or may obtain a solution of several functions by using a continuous spectrum of wavelengths at a continuous section of visible light region.

Obtaining a solution y of the relation function is described as follows. For convenience, the solution of the function, i.e., profile of the surface of the second substrate 10, as described with reference to FIG. 4 is described with reference to a real-time spectra obtained from about 100 points on the surface of the second substrate 10 by using a monochromatic spectrum of about 350 nm.

For example, FIG. 4 illustrates calculation of a solution of a linear function using a spectrum in the real-time spectrum analysis server 220, which may calculate a solution corresponding to a layer material state by using a constant value or fixed value such as 'w' and 'b' provided from the reference spectrum analysis server 120. Here, a linear function is used as the relation function corresponding to a state, i.e., CD, thickness or recess, of the real-time layer material. For example, if Equation 1 is rewritten as y1=f(w1x1+b1), the linear function in FIG. 4 may be written in a matrix form, i.e., each of w, x, b, and y may be represented by a matrix. A solution of the linear function in FIG. 4 may be represented by Equation 2 below.

$$y_{11}=w_{11}x_{11}+w_{12}x_{21}+\ldots+b_{11}$$

$$y_{12}=w_{11}x_{12}+w_{12}x_{22}+\ldots+b_{12}$$

$$y_{21}=w_{21}x_{11}+w_{22}x_{21}+\ldots+b_{21} \qquad \text{Equation 2}$$

In Equation 2, $y_{11}$ indicates a solution of function corresponding to a layer material profile of '1' at a position of '1', and $x_{11}$ indicates a spectrum having a specific wavelength, i.e., 350 nm, corresponding to a layer material profile of '1' at a position of '1', $w_{11}$ denotes a fixed value corresponding to a layer material profile of '1' at a position of '1', and $b_{11}$ denotes a constant value corresponding to a layer material profile of '1' at a position of '1'. For example, the layer material profile of '1' may refer to thickness, and a layer material profile of '2' and '3' may refer CD and recess, respectively. Accordingly, e.g., $y_{11}$ may refer to the layer material profile with respect to thickness at a position of '1', and $y_{21}$ and $y_{31}$ refer to the layer material profile with respect to thickness at position '2' and '3', respectively.

The Equation 2 provides that $y_{11}$ is influenced by $x_{12}$, $x_{13}$ ... spectra in addition to the $x_{11}$ term, which is why a continuity for a measurement target is partially provided at a corresponding position and which is why to provide a continuousness of measurement target through diffraction or refraction of incident light and reflected light from optical device 210. Thus, a solution of function for $y_{11}$ is calculated with respect to not only a real-time spectrum of a real-time layer material profile $x_{11}$, but also with respect to real-time spectra corresponding to the real-time layer material profile of $x_{12}x_{13}$ at corresponding positions.

For example, to obtain a thickness profile of a real-time layer material in a deposition process, a corresponding position has only a single profile. Thus, a solution of function of a single matrix, i.e., an array including one row and a plurality of columns, may be obtained. Calculating a fixed value and a constant value corresponding to a 'w' matrix and a 'b' matrix will be described below through an analysis method using the reference spectrum analysis server 120.

Figure 5A:
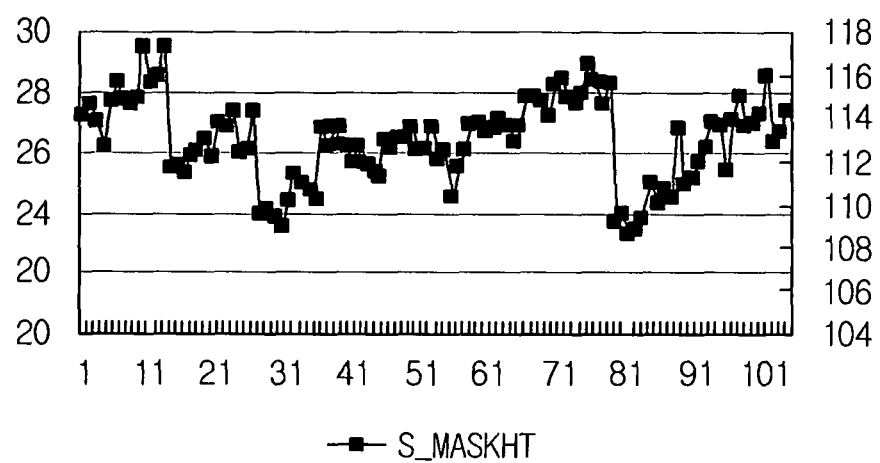
FIGS. 5A to 5C illustrate graphs representing a profile of a substrate surface calculated through a linear function having a spectrum as a variable.
Figure 5B:
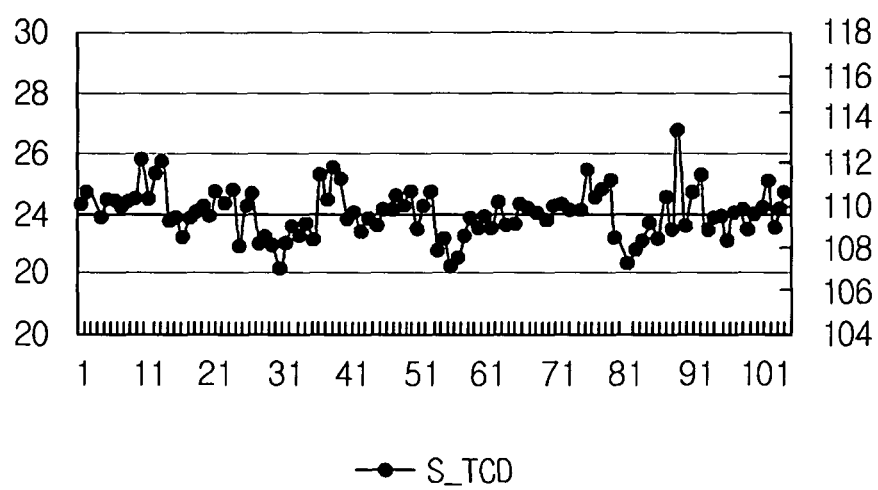
Figure 5C:
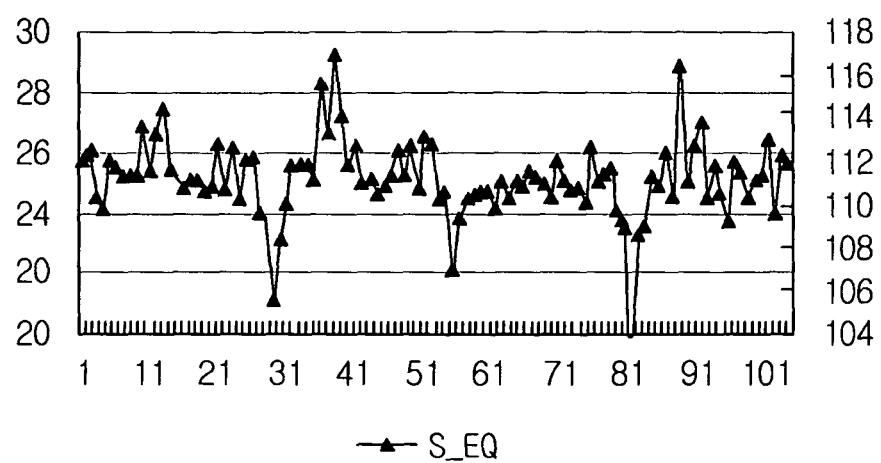

FIGS. 5A to 5C illustrate graphs obtained by calculating a profile of a real-time layer material on the surface of the second substrate 10 through a linear function having a real-time spectrum as a variable, i.e., 'x' in FIG. 4. The graphs in FIGS. 5A to 5C illustrate height MASKHT of the real-time layer material, e.g., a mask layer on the second substrate 10, top CD value S_TCD, and a CD difference value S_EQ of positioned Nos. 1 to 100 on the second substrate 10. Here, a unit of the horizontal axis is nm to represent position numbers, the right vertical axis represents values corresponding to the level of height of the mask layer, and the left vertical-axis represents values corresponding to a level of CD difference and top CD. As illustrated in FIG. 5, the height values of the mask layer are distributed within the range of about 108 nm to about 118 nm, and the top CD value and CD difference values are evenly represented within the range of about 20 nm to about 30 nm. The CD difference value designates a difference between a bottom CD value and the top CD value.

Therefore, in a layer material dimension analysis method according to an embodiment, a profile of the surface of the second substrate 10 may be detected in real time by obtaining a solution of corresponding function applied to a semiconductor manufacturing process of the second substrate 10.

Referring back to FIG. 3, when the calculation of function using a real-time spectrum is completed in the real time spectrum analysis server 220, it may be checked in operation S50 whether an entire layer-material dimension analysis of the second substrate 10 has been completed. For example, if the analysis is complete and a solution of function is input to the host computer 300, the host computer 300 may monitor a normal state of semiconductor manufacturing process of the second substrate 10.

When the surface analysis of the second substrate 10 in operation S50 is completed, the second substrate 10 may be unloaded in operation S60, so a subsequent semiconductor manufacturing process may be performed. When the surface analysis of the second substrate 10 in operation S50 is not completed, the sequence of operations S20 to S50 may be repeated.

Accordingly, a solution of function may be obtained by using a real-time spectrum as a variable in a layer material dimension analysis method according to an embodiment, thereby analyzing a profile of the real-time layer material on the second substrate in real time. Therefore, productivity may be increased.

A determination for a function relation between the reference spectrum 102 and the reference profile 104 in the reference spectrum analysis system 100 is described as follows. It is noted that the analysis of the reference spectrum 102 must be performed before the real-time spectrum analysis during processing in order to provide the determined function relation for the real-time spectrum analysis. As described above, the kinds of determined functions, i.e., the types of function relation between the reference spectrum 102 and the reference profile 104, may be different from each other according to semiconductor manufacturing processes processing the first substrate, i.e., the reference substrate, and the second substrate 10.

The reference spectrum analysis method according to a first embodiment will be described hereinafter with reference to FIG. 6. In particular, the first embodiment is directed toward selection of a linear function and obtaining fixed and constant values for the linear function.

Figure 6:
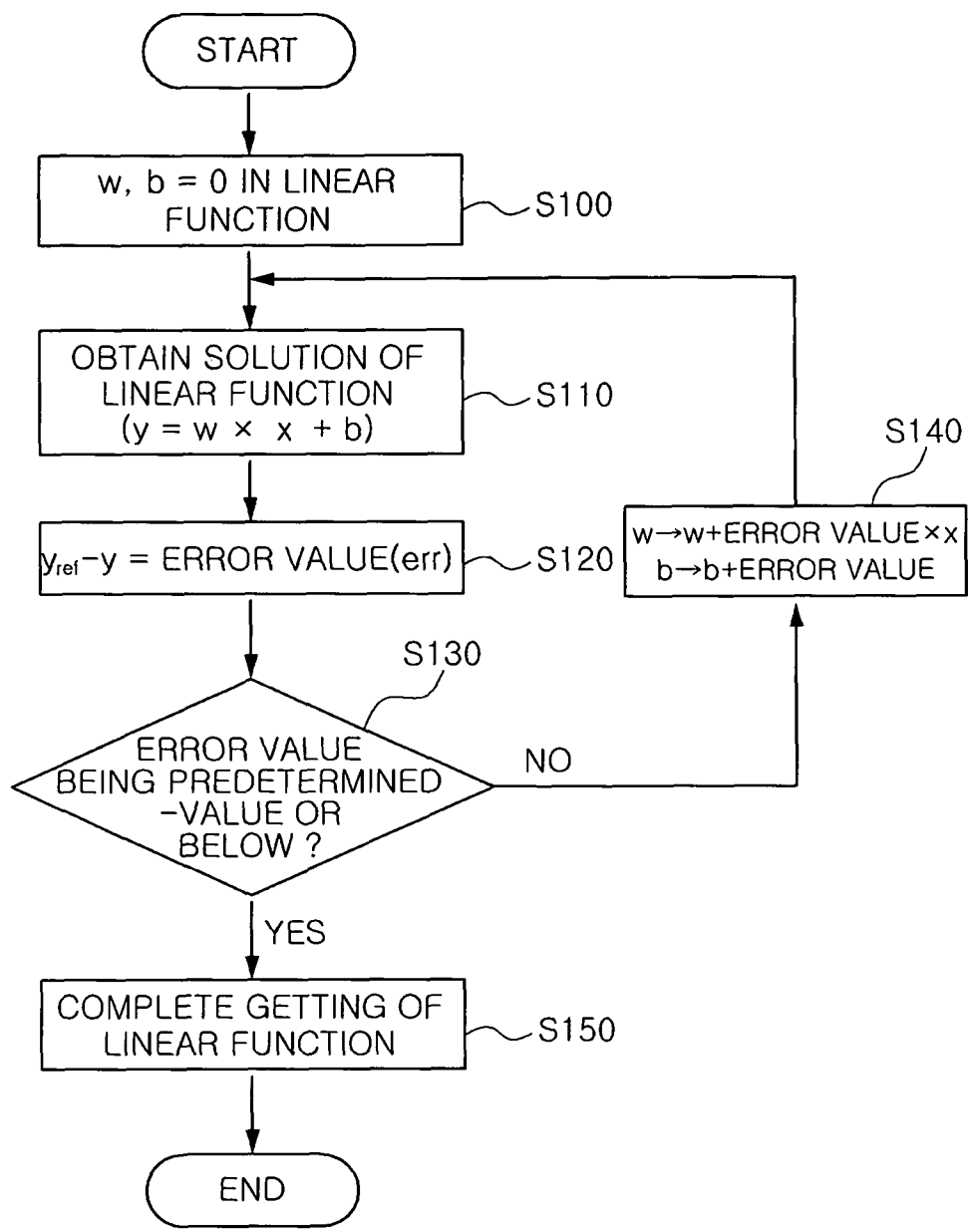
FIG. 6 illustrates a flowchart of a method for acquiring a constant value and a fixed value of a linear function selected in a reference spectrum analysis method according to a first embodiment.

FIG. 6 illustrates a flowchart for obtaining fixed and constant values, i.e., linear fixed value, for the linear function to be used in the reference spectrum analysis method of the first embodiment. As illustrated in FIG. 6, the values may be obtained heuristically.

As shown in FIG. 6, the reference spectrum analysis server 120 may first optionally provide '0' as a fixed value and a constant value for the linear function, in operation S100. In other words, as illustrated in FIG. 6, the fixed and constant values 'w' and 'b' may be optionally initialized and set as '0'.

Then, in operation S110, the fixed and constant values 'w' and 'b' and the reference spectrum 102, i.e., as the x variable, may be used in Equation 1 to obtain a y-value corresponding to a solution of the linear function. It is noted that the y-value calculated via Equation 1 in operation S110 is different than $y_{ref}$, i.e., reference profile 104.

Subsequently, the y-value corresponding to the solution of the linear function is subtracted from $y_{ref}$ to calculate an error value, in operation S120. Here, the error value may be provided through a comparison of the reference profile 104 and the solution of the linear function.

Further, in operation S130, the error value calculated in operation S120 may be compared to a predetermined value, e.g., a fixed value of about 0.001 or lower, to determine whether the error value is sufficiently small. The predetermined value may be optionally set to any suitable value. For example, if the error value calculated in operation S120 must converge to about '0', the predetermined value may be set as 0.001 or lower.

In operation S140, when the error value calculated in operation S120 equals the predetermined value or more, the fixed value 'w' may be fed back to the linear function by multiplying the calculated error value by the reference spectrum 102 and adding a previous fixed value 'w' thereto. For example, as illustrated in FIG. 6, when the error value is larger than 0.001, the fixed value w may be recalculated, e.g., $w_{new}$=w+(error value)*x. Similarly, the constant value 'b' may be fed back to the linear function by adding the calculated error value to a previous constant value 'b', e.g., $b_{new}$=b+(error value). Accordingly, $w_{new}$ and $b_{new}$ may be used in operation S110 to calculate a new y-value corresponding to a solution of the linear function. The sequence of operations S110 to S140 may be repeated until the values $w_{new}$ and $b_{new}$ provide a y-value, i.e., a solution to the linear function, that has an error value below, e.g., about 0.001, as compared to $y_{ref}$.

Finally, in operation S150, when the calculated error value drops to the predetermined value or below and the feedback operation is completed, the fixed value 'w' and constant value 'b' of the linear function are acquired, i.e., the values w and b that provided a y-value with an error value below, e.g., about 0.001.

The feedback operation, i.e., sequence of operations S110 to S140, may be performed repeatedly tens to hundreds of times, thereby making the fixed value 'w' and constant value 'b' of the linear function constant. Here, the fixed value 'w' and constant value 'b' of the linear function may be represented as the matrix described above.

Figure 7:
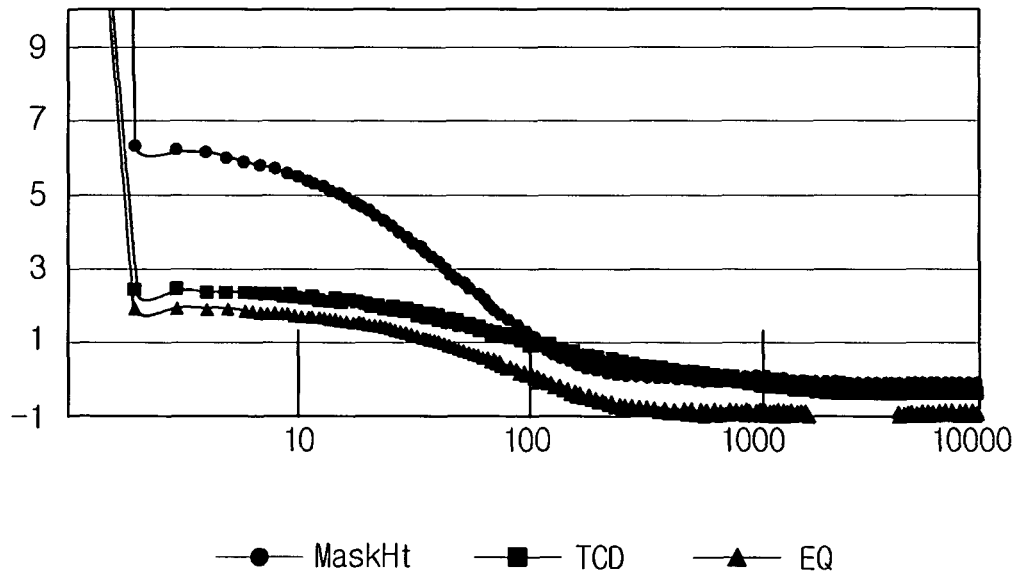
FIG. 7 illustrates a graph representing a change of error function obtained from a reference spectrum analysis server.

FIG. 7 illustrates a graph of a change in the error value obtained from the reference spectrum analysis server 120. As illustrated in FIG. 7, feedback operations to calculate the fixed value 'w' and the constant value 'b' for the linear function were performed about 500 times to about 1000 times or more until the error value converged to about '0'. Here, the horizontal axis compressively denotes the number of feedback operations, and the vertical axis denotes the error value. As further illustrated in FIG. 7, although there are little differences between the convergence of the error value with respect to the type of surface profile, i.e., CD difference values S_EQ, top CD values S_TCD and height values MASKHT of mask layers with mutually difference sizes of reference spectrums 102, it appears that the error value converged to about '0' as the feedback operations progressed. Therefore, as the feedback operations are performed until the error value is approximated to '0', the fixed value and the constant value of the linear function may be decided.

Figure 8A:
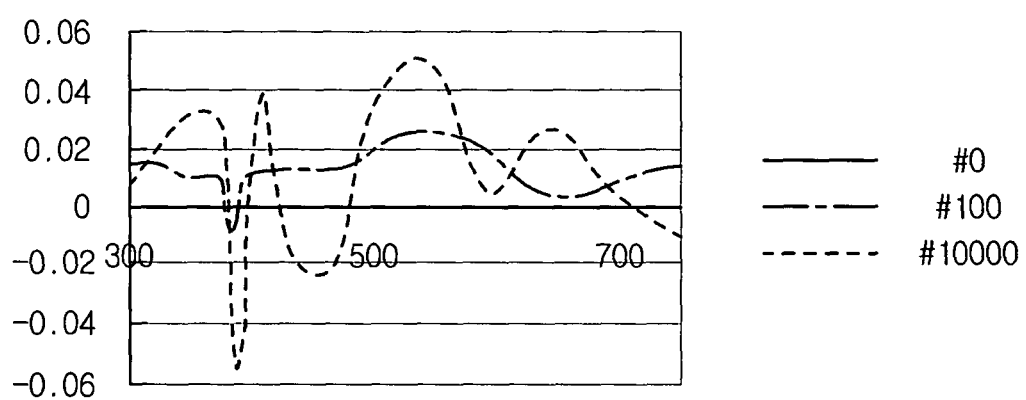
FIGS. 8A and 8B, 9A and 9B, and 10A and 10B illustrate graphs of respective fixed and constant values of a linear function varied by the number of feedback operations therein to obtain a mask height value, a top CD value, a and CD difference value, respectively.
Figure 8B:
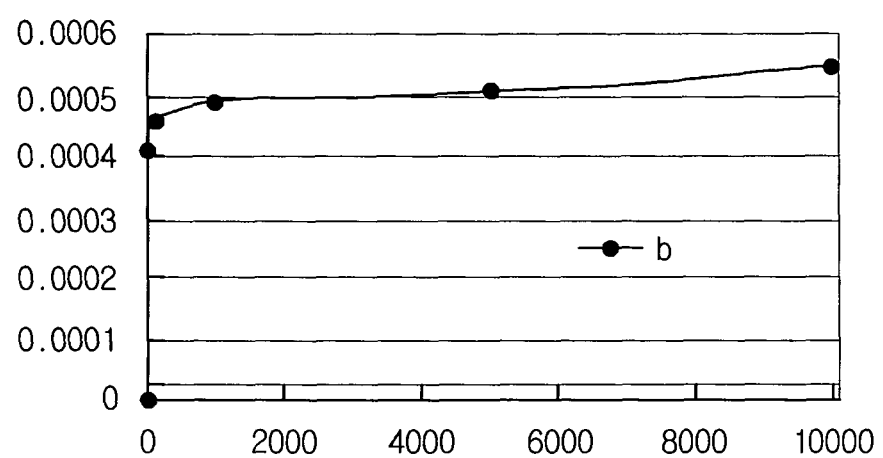
Figure 9A:
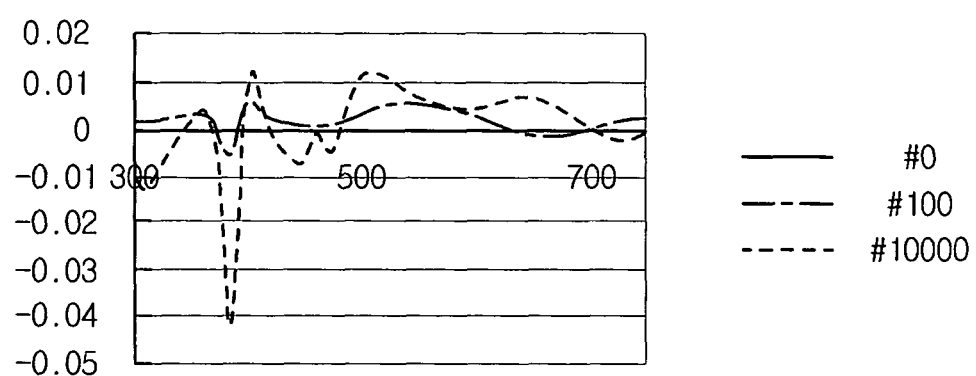
Figure 9B:
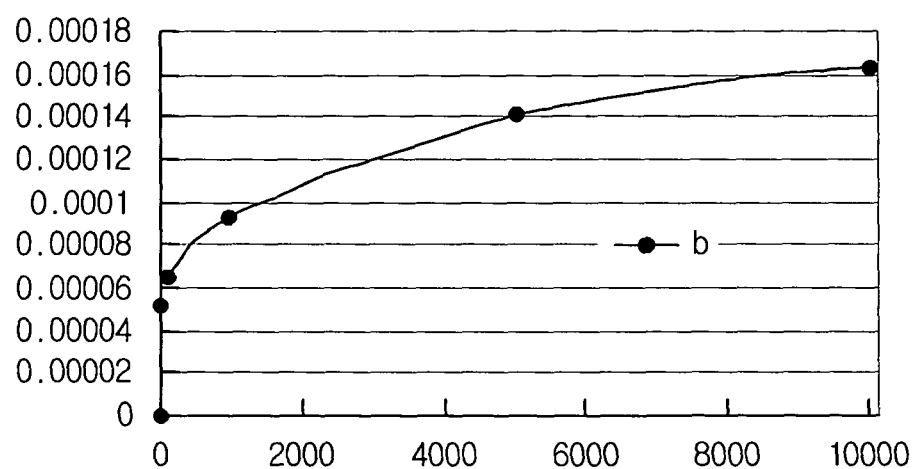
Figure 10A:
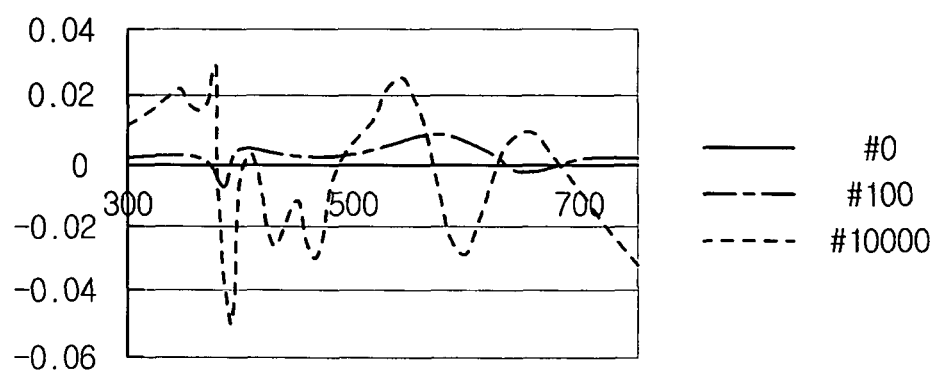
Figure 10B:
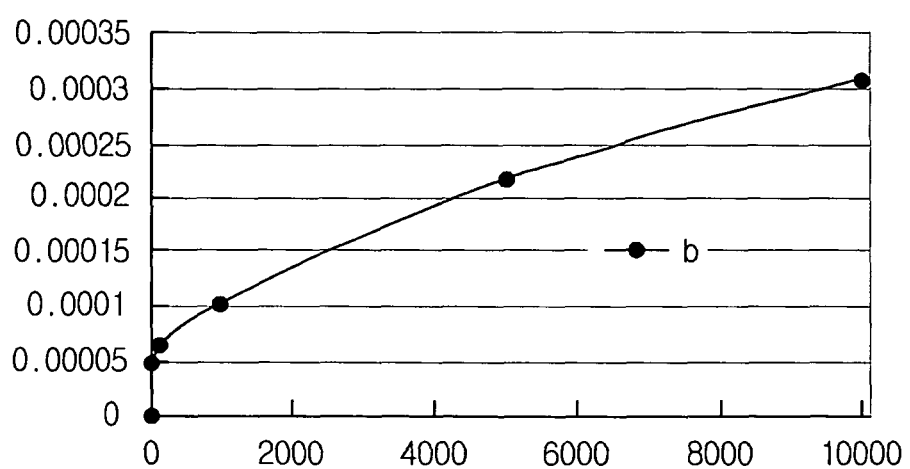

FIGS. 8A and 8B illustrate respective graphs of the fixed value 'w' and the constant value 'b' of the linear function varied by the number of feedback operations to obtain a mask height value. FIGS. 9A and 9B illustrate respective graphs of the fixed value 'w' and the constant value 'b' of the linear function varied by the number of feedback operations to obtain a top CD value. FIGS. 10A and 10B illustrate respective graphs of the fixed value 'w' and the constant value 'b' of the linear function varied by the number of feedback operations to obtain a CD difference value.

As shown in FIGS. 8A, 9A, and 10A, the fixed value 'w' of the linear function is represented as a very small value on the periphery of '0' according to a wavelength change of the spectrum. Here, the horizontal axis indicates a wavelength of the real-time spectrum, and the vertical longitudinal axis indicates the value of the fixed value 'w'. Further, the legend on right side of the graphs in FIGS. 8A, 9A, and 10A provide a feedback number of the error value, i.e., a number of repeated feedback operations to obtain the minimal error value. As the feedback number increases, the fixed value 'w' of the linear function is converged to a relatively stable value. Thus, the fixed value 'w' of the linear function may be proportional to the real-time spectrum, and may be changed depending on the varying wavelengths of the real-time spectrum. Meanwhile, it is noted that the constant value 'b' of the linear function may be affected relatively less by the change of the spectrum.

As shown in FIGS. 8B, 9B, and 10B, the constant value 'b' of the linear function is changed independently of the spectrum, and thus, there is shown a partial change based on the number of feedback operations, partially depending on the error value. Here, the horizontal axis denotes the number of feedback operations, and the vertical axis denotes the level of the constant value 'b'.

Figure 11:
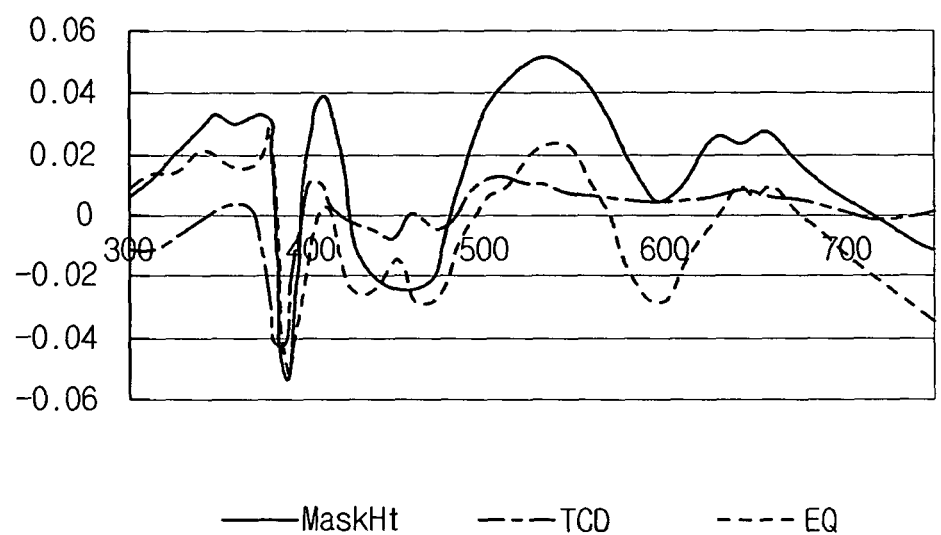
FIG. 11 illustrates a graph of overlapping fixed values of a linear function to get a mask height value, top CD value, and CD difference value.

FIG. 11 illustrates a graph of overlapping fixed values 'w' of the linear function for the mask height value, top CD value, and the CD difference value. As illustrated in FIG. 11, the fixed values 'w' of the linear function have similar peaks and shapes based on a wavelength band of a spectrum. Here, the fixed values 'w' are obtained through about 1000 feedback operations. Further, constant values 'b' of the linear function for the mask height value, top CD value, and CD difference value through the same feedback operation number may be each applied as 0.0005, 0.002, 0.0003.

Figure 12A:
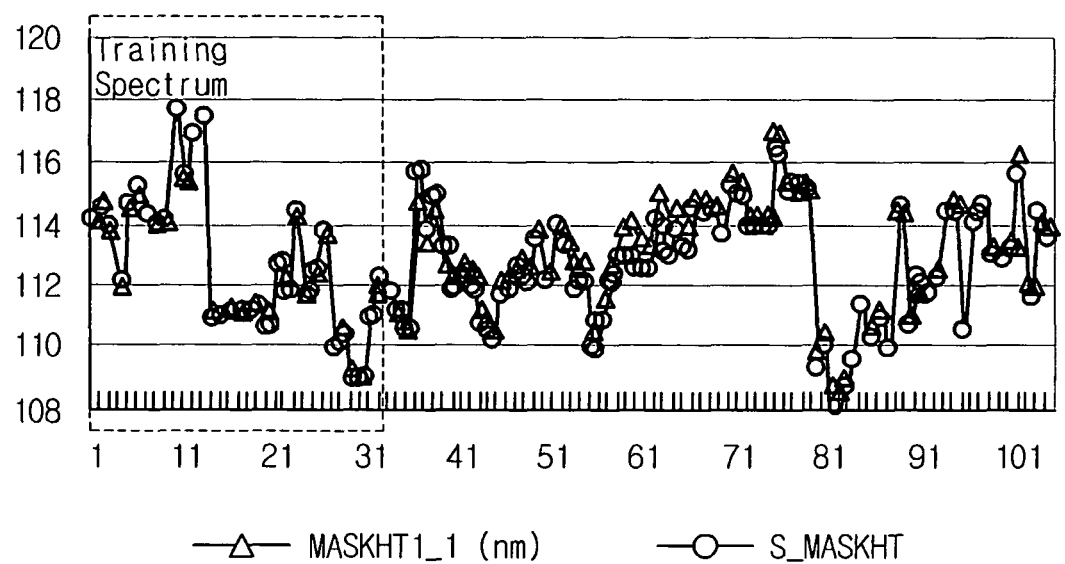
FIGS. 12A to 12C illustrate graphs representing a comparison between an actual profile and a solution of a linear function to which fixed and constant values are provided at 350 nm band shown in the graph of FIG. 11.
Figure 12B:
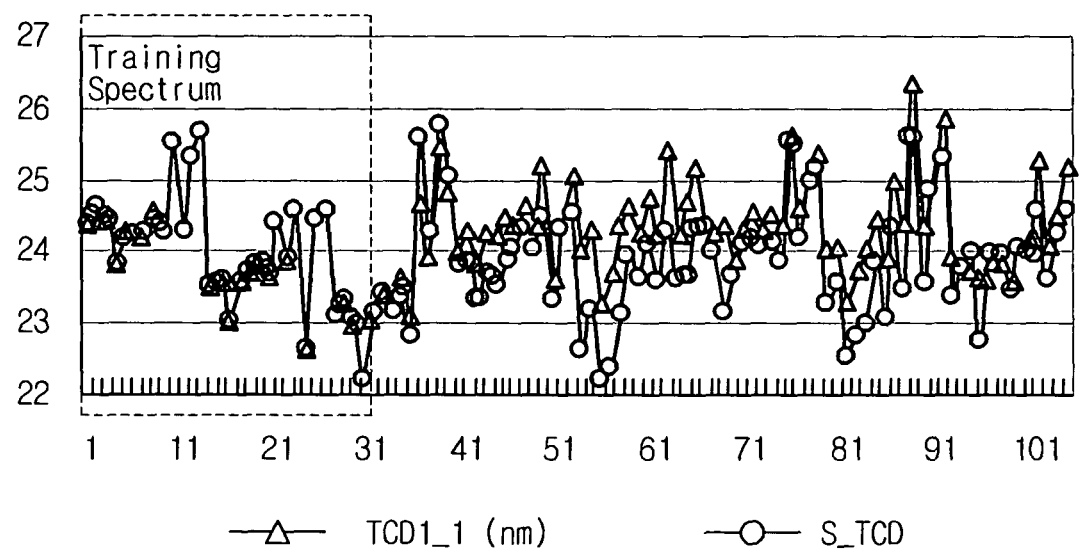
Figure 12C:
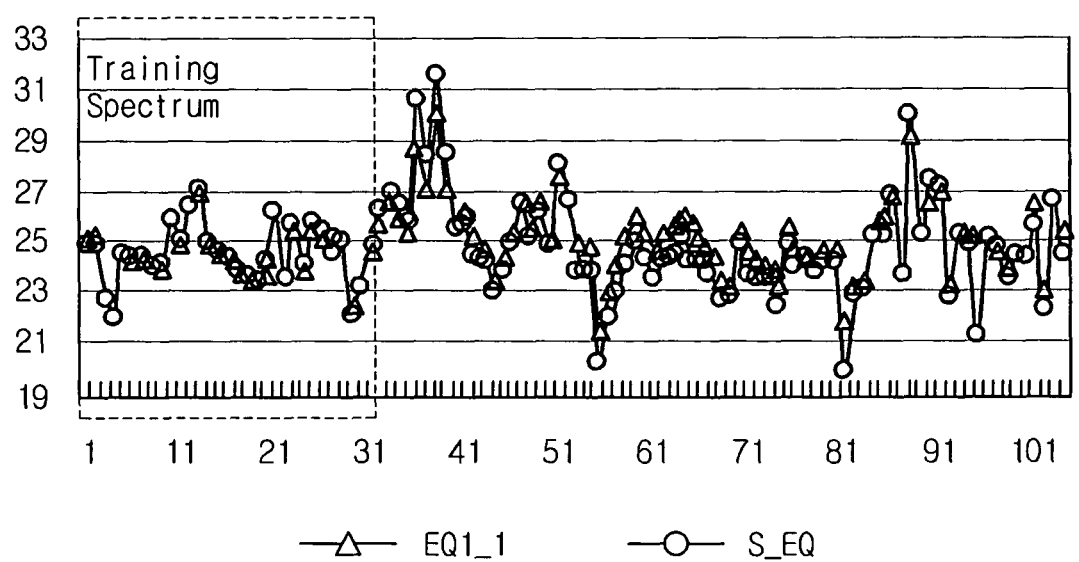

FIGS. 12A to 12C illustrate graphs comparing an actual profile and a corresponding solution of a linear function with fixed and constant values. The solution of the linear function was provided at 350 nm band shown in FIG. 11. The calculated solution is indicated as S_MASKHT, S_TCD, and S_EQ, and the actual profile is indicated as MASKHT1_1, TCD1_1, and EQ1_1. Respective values of the solution and the actual profile are almost equal in about 30 points of the second substrate 10. In particular, referring to FIG. 12A illustrating a comparison of the solution to the actual profile corresponding to a height of the mask layer, there is provided an almost similarity between the solution S_MASKHT of the linear function and the profile MASKHT1_1 of the actual mask height even in more than 30 points. This indicates that the linear function may be an appropriate function when obtaining a thickness of layer material.

Accordingly, in the reference spectrum analysis method according to the first embodiment, a complete linear function may be obtained by feeding back a solution of the linear function using the reference spectrum 102 as a variable, the error value as a difference between the reference profile 104 and the solution, and the constant value and fixed value of the linear function, thereby realizing the real-time reference spectrum analysis method.

A method of analyzing the reference spectrum 102 according to a second embodiment of the invention is provided to mix an exponential function and a linear function, and thus, obtain fixed values, i.e., exponential fixed value ($w_n$) and linear fixed value (w) and constant value (b).

Figure 13:
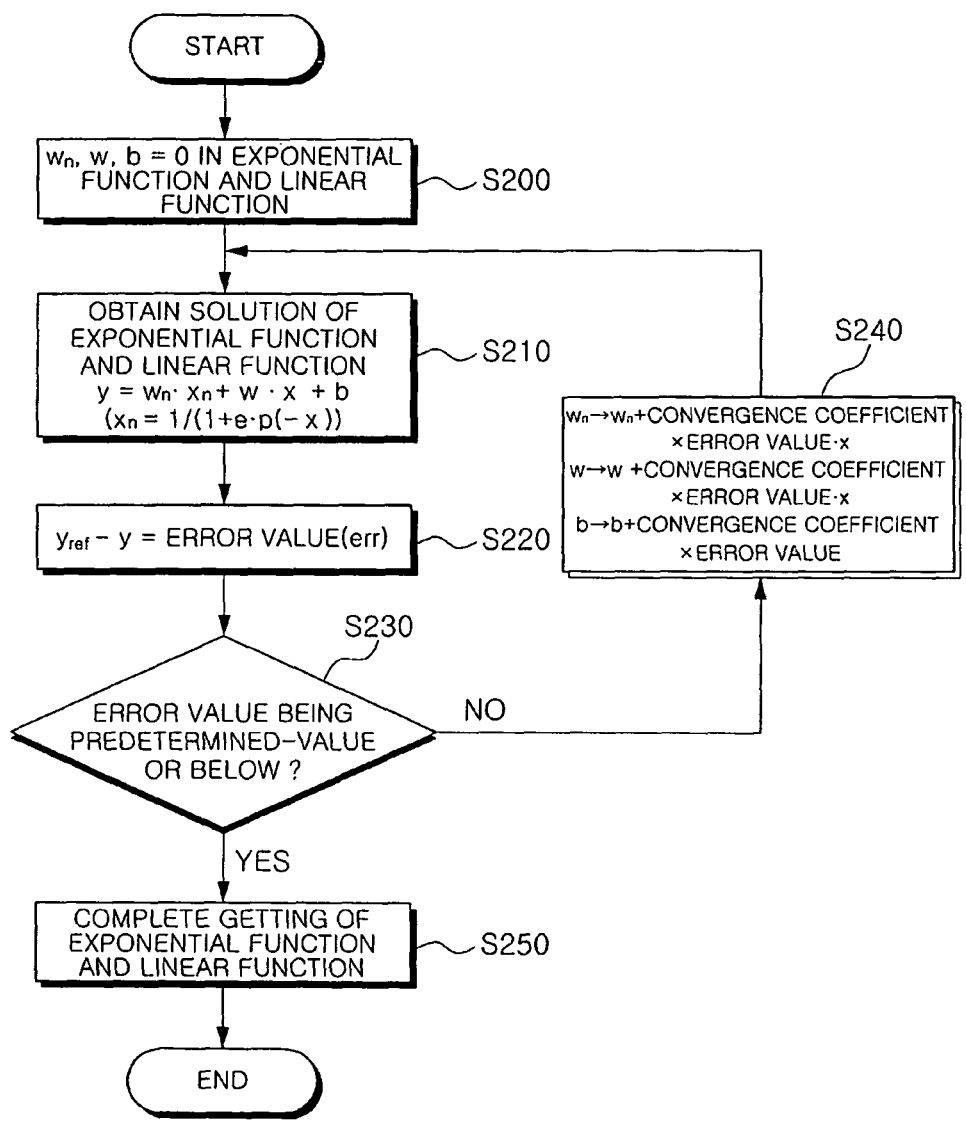
FIG. 13 illustrates a flowchart of a method for acquiring fixed values and a constant value of exponential and linear functions selected in a reference spectrum analysis method according to a second embodiment.

FIG. 13 illustrates a flowchart to acquire fixed and constant values of an exponential function and a linear function selected in the reference spectrum analysis method according to the second embodiment of the invention.

As shown in FIG. 13, reference spectrum analysis server 120 may optionally provide '0' as fixed values ($w_n$, w) and a constant value (b) of the exponential function and the linear function in operation S200.

Then, a y-value may be obtained by entering a spectrum as an x value of the linear function in operation S210. As illustrated in FIG. 13, it is noted that the y-value may include a solution to an addition of two terms. The first term is a product of a fixed value and an exponential function and the second term is a linear function.

After that, an error value may be obtained by subtracting the calculated y-value from a reference y value corresponding to the reference profile 104 in operation S220. Here, the error value may be provided through a comparison of the reference profile 104 and a solution of the linear function.

It is then checked in operation S230 that the error value drops below an optionally predetermined value, e.g., 0.001. Here, the error value may converge to about '0'.

Subsequently, when the error value is a predetermined value or more, the fixed values ($w_n$, w) may be fed back to the function after multiplying convergent coefficient, error value and spectrum, and then adding a previous fixed value ($w_n$, w) thereto. The constant 'b' value may be fed back to the function by adding a product of the convergent coefficient and error value to a previous constant value 'b' in operation S240. Here, the convergent coefficient (correlation coefficient) is a coefficient to be multiplied by the error value so as to get a convergence of the fixed values ($w_n$, w) and the constant value (b) in the feedback.

Figure 14:
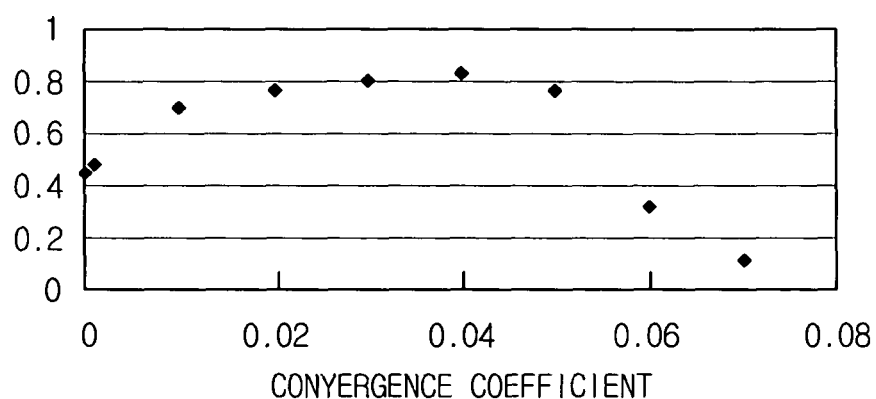
FIG. 14 illustrates a graph representing the relationship between a convergent coefficient of FIG. 13 and a normalized value of a product of an error value and a spectrum.

FIG. 14 illustrates a graph providing the relationship between a convergent coefficient of FIG. 13 and a normalized value of a product of an error value and a spectrum. The convergent coefficient is for a convergence of a product of the error value and spectrum, and a value of about 0.04 may be an optimum value to reach the normalized value approximate to 1. Here, a horizontal axis of FIG. 14 denotes a convergent coefficient as a variable, and a vertical axis denotes a normalized value of a product of an error value and a spectrum. As shown in FIG. 14, a normalized value is highest when the convergent coefficient equals about 0.04 as also illustrated in Table 1 below.

TABLE 1

| Convergent coefficient (cc) | Normalized value ($R^2$) |
|---|---|
| 0.0001 | 0.4467 |
| 0.001 | 0.4789 |
| 0.01 | 0.6959 |
| 0.02 | 0.7614 |
| 0.03 | 0.7928 |
| 0.04 | 0.8121 |
| 0.05 | 0.7577 |
| 0.06 | 0.3149 |
| 0.07 | 0.1143 |
| 0.1 | none value |

As illustrated in Table 1, a normalized value is relatively highest at 0.04 of the convergent coefficient. Though not shown in the drawing, application of a higher sampling number of the reference spectrums 102 to obtain a convergent coefficient may be better, and higher feedback numbers may be better.

Accordingly, the convergent coefficient may be multiplied by the error value through the feedback, i.e., tens to hundreds of times, thereby setting values for the fixed values ($w_n$, w) and constant value (b) of the exponential and linear functions, i.e., even and uniform values. The fixed values ($w_n$, w) and the constant value (b) of the exponential and linear functions may be fed back until the error value reaches about '0' by using a change of error function described above in the reference spectrum analysis method according to the first embodiment.

Figure 15A:
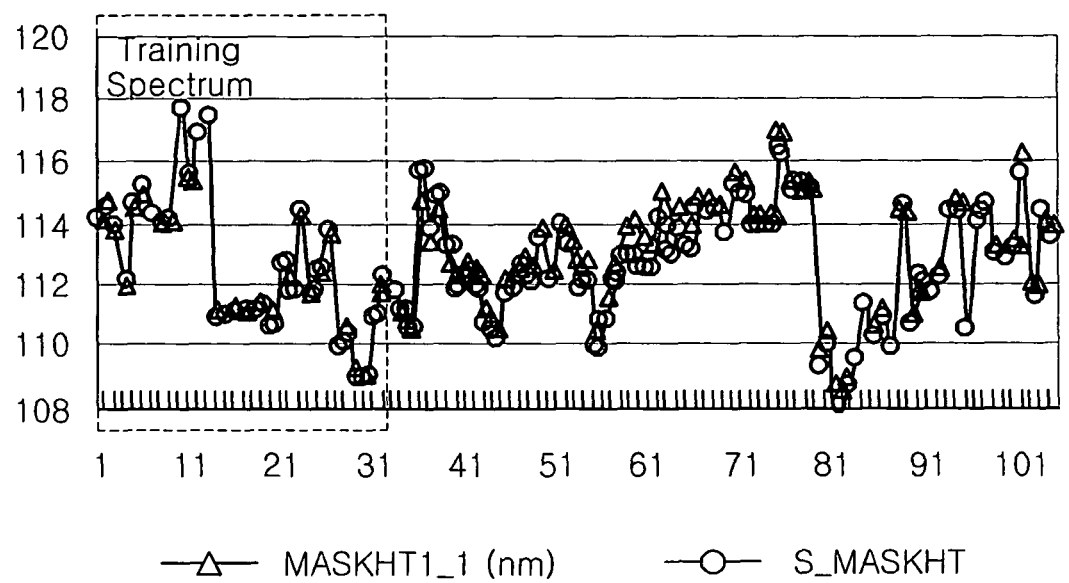
FIGS. 15A to 15C illustrate graphs representing a comparison between an actual profile and a solution of a function corresponding to a mask height value, top CD value, and CD difference value obtained by using fixed values and constant value of exponential and linear functions calculated through a reference spectrum analysis method according to a second embodiment.
Figure 15B:
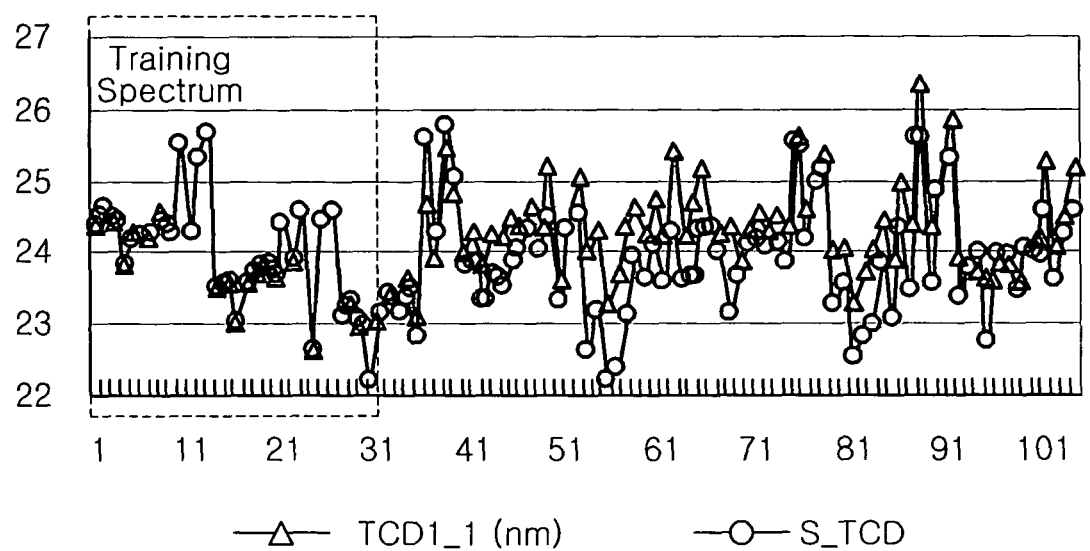
Figure 15C:
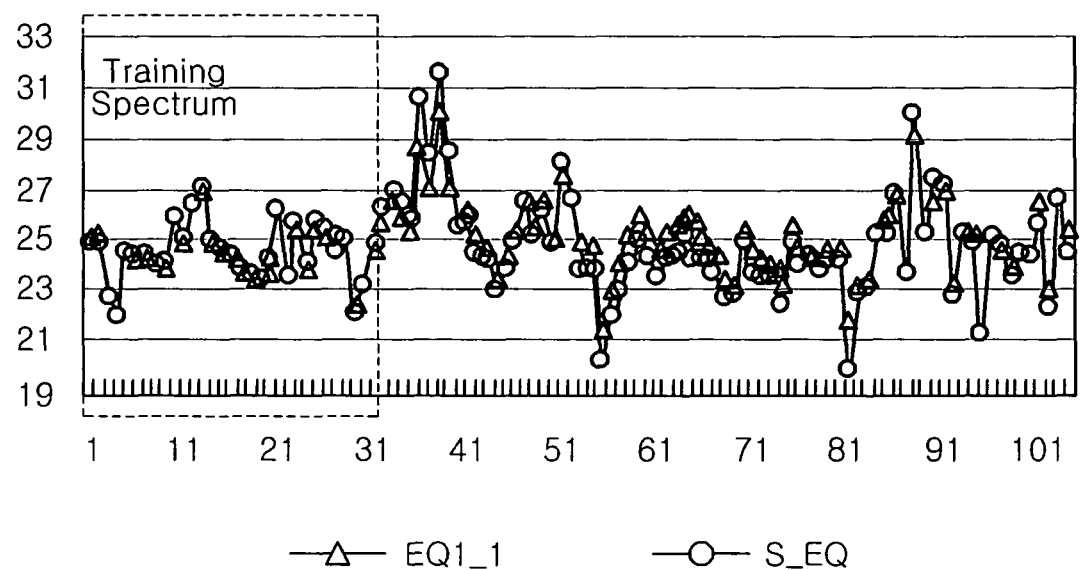

FIGS. 15A to 15C illustrate graphs obtained by comparing an actual profile to a solution of function corresponding to the mask height value, top CD value, and CD difference value according to the reference spectrum analysis method of the second embodiment.

As shown in FIGS. 15A to 15C, solutions, i.e., S_MASKHT, S_TCD, S_EQ, of exponential and linear functions with a spectrum as a variable, and actual profile, i.e., MASKHT1_1, TCD1_1, EQ1_1, were almost equal to each other at about 30 points of the second substrate 10. Furthermore, relatively better result was provided to 100 points after that in the first embodiment of the invention. In view of FIG. 15C that illustrates substantially similar values for S_EQ and EQ1_1 with respect to the exponential and linear functions, a CD of layer material formed through an etching process or a profile corresponding to a recess may be appropriately analyzed through the exponential and linear functions.

Finally, when the error value falls to a predetermined value or below, the fixed and constant values of the exponential and linear functions may be decided in operation S250.

Accordingly, in the reference spectrum analysis method according to the second embodiment, a solution of the linear and exponential functions using the reference spectrum 102 as a variable, and an error value as a difference from the reference profile 104, may be fed back to the fixed and constant values of the exponential and linear functions, thereby obtaining a complete function to perform the real-time spectrum analysis through the real-time spectrum analysis server 220.

In apparatus and method of manufacturing semiconductor devices according to embodiments, computation of a profile of a three-dimensional pattern, i.e., a relatively complicated and time-consuming computation as compared with a computation of a two-dimensional pattern, may be simplified by applying a spectrum detected in real time to a function computed through reference data, so a solution of the function may correspond to the profile of the three-dimensional pattern. In addition, the apparatus and method of manufacturing semiconductor devices may monitor a semiconductor manufacturing process in real time by providing a substantially reduced profile computation time by employing the solution of the function, i.e., a function including spectrum detected in real time as a variable, as a profile of a substrate surface.

It will be apparent to those skilled in the art that modifications and variations can be made in the present invention without deviating from the inventive spirit or scope. Thus, it is intended that the present invention cover any such modifications and variations of this invention provided they come within the scope of the appended claims and their equivalents. For example, manufacturing processes of a semiconductor manufacturing apparatus are included in the embodiments of the invention, and their enlarged application is available. Further, although a method of analyzing a dimension of layer material formed on a second substrate has been described above according to an embodiment, a semiconductor manufacturing method including that may be applied thereto. Additionally, a dimension analysis method of layer material formed on a substrate formed of glass, plastic, wood material with a general macro surface process besides a semiconductor manufacturing method with a micro surface process may be applied thereto. Accordingly, these and other changes and modifications are seen to be within the inventive true spirit and scope as defined by the appended claims.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A semiconductor manufacturing apparatus, comprising:
    a semiconductor process device configured to process a target substrate;
    a reference spectrum analysis system configured to detect a reference spectrum and to detect a reference profile for a reference substrate, the reference spectrum analysis system being configured to determine a relation function between the detected reference spectrum and the detected reference profile; and
    a real-time spectrum analysis system configured to detect a real-time spectrum of the target substrate and to apply the calculated relation function to the detected real-time spectrum in real-time for a real-time profile of the target substrate, the reference spectrum analysis system and real-time spectrum analysis system being configured to use an empirical spectrum analysis.

2. The apparatus as claimed in claim 1, wherein the reference spectrum analysis system and the real-time spectrum analysis system are separate systems with separate optical devices, the reference spectrum analysis system including a reference optical device and a measurement device, the reference optical device being configured to detect the reference spectrum from a light reflected by irradiating an incident light onto a surface of the reference substrate, and the measurement device being configured to measure the reference profile of a surface of the reference substrate.

3. The apparatus as claimed in claim 1, wherein the real-time spectrum analysis system is configured to determine the real-time profile of the target substrate based only on calculations with respect to the calculated relation function as determined by the reference spectrum analysis system, without separate three-dimensional measurements of the real-time profile of the target substrate.

4. The apparatus as claimed in claim 2, wherein the reference spectrum analysis system further comprises a reference spectrum analysis server, the reference spectrum analysis server being configured to determine the relation function between the detected reference spectrum and the detected reference profile, and the relation function being based only on the detected reference spectrum and profile.

5. The apparatus as claimed in claim 4, wherein the reference spectrum analysis server is configured to determine the relation function as a linear function, when the semiconductor process device performs a deposition process on the target substrate, and the reference spectrum analysis server is configured to determine the relation function as an exponential function, when the semiconductor process device performs an etching process on the target substrate.

6. The apparatus as claimed in claim 4, wherein the real-time spectrum analysis system includes a real-time spectrum analysis server separate from the reference spectrum analysis server, the real-time spectrum analysis server being configured to apply the real-time spectrum to the relation function and to determine a three-dimensional profile of a structure on the target substrate based on the relation function, the real-time spectrum being detected from a light reflected by irradiating an incident light from the optical device to the target substrate.

7. The apparatus as claimed in claim 6, further comprising a host computer configured to receive in real-time a drive state of the semiconductor process device according to the real-time profile of the target substrate.

8. A method of manufacturing a semiconductor device, comprising:
    performing a semiconductor manufacturing process of at least one reference substrate and at least one target substrate in a semiconductor process device;
    detecting a reference spectrum and a reference profile for the reference substrate;
    determining a relation function between the detected reference spectrum and reference profile;
    detecting a real-time spectrum of the target substrate, each of the detecting including an empirical spectrum analysis; and
    determining in real time a real-time profile of the target substrate processed in the semiconductor process device by using the detected real-time spectrum as a variable in the determined relation function.

9. The method as claimed in claim 8, wherein determining the real-time profile of the target substrate includes solving the relation function, the real-time profile of the target substrate corresponding to the solution of the relation function.

10. The method as claimed in claim 8, wherein:
    detecting the reference profile includes determining at least one of size, thickness, depth, and roughness of a layer material formed on the reference substrate, and
    determining the real-time profile includes three-dimensional characterization of a surface of the target substrate, based on the relation function.

11. The method as claimed in claim 8, wherein detecting the reference spectrum and the real-time spectrum includes using data corresponding to a ratio degree and a phase degree of light reflected from the reference and target substrates, respectively.

12. The method as claimed in claim 8, wherein determining the reference profile includes surface measurement using an electron microscope or an optical critical dimension technology using the reference spectrum.

13. The method as claimed in claim 9, wherein determining the relation function includes determining at least one of a linear function (primary function), a quadratic function, a higher-order function, a fraction function, a trigonometric function, an exponential function, and a logarithmic function.

14. The method as claimed in claim 9, wherein determining the relation function includes setting at least one relative fixed value and at least one constant value in the relation function via an error value calculation, wherein
    the error value is obtained by subtracting the solution of the relation function from the reference profile,
    the constant value is obtained by adding the error value to a previously calculated constant value,
    the relative fixed value is obtained by adding to a previously calculated relative fixed value a product of the error value and the reference spectrum, and
    repeatedly recalculating the error value, the constant value, and the relative fixed value until the error value equals a predetermined value or lower.

15. The method as claimed in claim 13, wherein determining the relation function includes selecting a linear function among a plurality of functions, when the real-time profile corresponds to a thickness of a layer material formed on the target substrate.

16. The method as claimed in claim 13, wherein determining the relation function includes selecting an exponential function among a plurality of functions, when the real-time profile corresponds to a recess or CD of a layer material formed on the target substrate.

17. The method as claimed in claim 14, wherein the relative fixed value and the constant value are represented as matrices.

18. The method as claimed in claim 14, wherein an initial value of each of the relative fixed value and the constant value is set as '0', such that the previously calculated relative fixed and constant values during a first recalculation of the relative fixed and constant values equal '0'.

19. The method as claimed in claim 14, wherein recalculating the relative fixed value and the constant value further comprises multiplying a convergent coefficient by the error value in a feedback execution.

20. A method of analyzing a profile of a layer material comprising:
  performing a semiconductor manufacturing process of a substrate;
  irradiating an incident light onto a surface of the substrate at a predetermined angle;
  detecting a spectrum of a light reflected from the surface of the substrate via an empirical spectrum analysis;
  determining a solution of a predetermined function by using the detected spectrum as a variable in the predetermined function; and
  monitoring a processing state of the surface of the substrate by using the solution of the predetermined function.

* * * * *